US007744522B2

(12) United States Patent
Vancraeyenest

(10) Patent No.: US 7,744,522 B2
(45) Date of Patent: Jun. 29, 2010

(54) SYSTEM FOR INFLUENCING OF A BIOLOGICAL CELLULAR STRUCTURE

(75) Inventor: Marc Vancraeyenest, Izegem (BE)

(73) Assignee: Letec NV, Bellegem (BE)

( * ) Notice: Subject to any disclaimer, the term of this patent is extended or adjusted under 35 U.S.C. 154(b) by 623 days.

(21) Appl. No.: 11/587,986

(22) PCT Filed: Mar. 24, 2005

(86) PCT No.: PCT/EP2005/003304
§ 371 (c)(1),
(2), (4) Date: Oct. 30, 2006

(87) PCT Pub. No.: WO2005/107866
PCT Pub. Date: Nov. 17, 2005

(65) Prior Publication Data
US 2008/0249349 A1 Oct. 9, 2008

(51) Int. Cl.
A61N 2/00 (2006.01)
(52) U.S. Cl. .............................. 600/9; 600/14
(58) Field of Classification Search ............... 600/9–15; 607/88–91
See application file for complete search history.

(56) References Cited
U.S. PATENT DOCUMENTS
6,520,903 B1 2/2003 Yamashiro 6,587,711 B1 * 7/2003 Alfano et al. ............... 600/476

FOREIGN PATENT DOCUMENTS
DE 3101715 9/1982
EP 0228537 7/1987
FR 2639834 6/1990

* cited by examiner

Primary Examiner—Charles A Marmor, II
Assistant Examiner—Carrie Dorna
(74) Attorney, Agent, or Firm—James Creighton Wray; Meera P. Narasimhan

(57) ABSTRACT

This invention relates to a system for influencing of a biological cellular structure, for instance, to generate a therapeutic effect in a human or animal body, making use of a combination of light energy and magnetic energy, said system being provided with at least one light source (2), (8), a magnetic energy source (12), which is preferably capable of generating a pulsing magnetic field, and devices to adjust and/or modulate the frequencies and/or phases and/or amplitudes of the light and/or the magnetic field so that resonances and/or interferences may be obtained in the biological cellular structure. The system preferably comprises a first (2) and a second light source (8), which generate light with a different coherence, in which the light coming from the first light source (2) and the light coming from the second light source (8) is preferably used alternately and/or with a phase shift and is polarized.

5 Claims, 5 Drawing Sheets

SYSTEM FOR INFLUENCING OF A BIOLOGICAL CELLULAR STRUCTURE

This application claims the benefit of Belgian Application No. 2004/0234 filed May 11, 2004 and PCT/EP2005/003304 filed Mar. 24, 2005, which are hereby incorporated by reference in their entirety.

BACKGROUND OF THE INVENTION

This invention relates to a system for influencing a biological cellular structure, in which use is made of a combination of light energy and magnetic energy.

This invention relates in particular to a system for realising beneficial effects on a biological cellular structure in a human, an animal or a plant. More in particular, it relates to a system for realizing specific therapeutic effects in humans and animals.

It has long been known that light of certain frequencies can create certain therapeutic effects on a living creature. Applications thereof are generally indicated by the term light therapy. There are instruments for application of light therapy that comprise a so-called coherent light source, such as a laser system. These systems have the disadvantage that their use can be hazardous. Other well-known instruments comprise a source of incoherent light, such as a full-spectrum lamp.

Besides these, also the magnetic field therapy is known, in which magnetic energy is used to obtain a beneficial influence on the health of the human.

In addition, instruments that combine the effects of light therapy and magnetic energy have already been developed. Such device is described in a number of patent publications, as for instance in French patent application No. 2 639 834. In this document, an instrument is described by which pain, inflammation and local energy disturbances can be treated. With this instrument, light of a certain spectrum as well as a magnetic or an electric field can be realised. This instrument allows orienting the so-realised electrical and magnetic fields in relation to the treated tissue. This kind of instruments has only a very limited number of fields of application and they are furthermore not very effective.

In European patent publication EP 0 228 537 A2 and in German patent publication DE 3 101 715 A1, instruments are described with which we can combine light therapy with a treatment with magnetic energy. In such treatment, we obtain at the most a combination of the known effects of infrared light therapy and the known effects of the magnetic field therapy.

In addition, the presently known instruments have the disadvantage that the light energy cannot penetrate deep enough (at the most a few mm) in the tissue, so that the efficiency of these instruments leaves much to be desired. Their therapeutic effect is rather minimal and within a very limited field of application. Their field of application is most often limited to tissue heating and pain relief.

SUMMARY OF THE INVENTION

The object of this invention is to realise a system by which, when influencing a biological cellular structure, greater efficiency is obtained through a combination of light energy and magnetic energy and this within a very broad field of application, This objective is obtained because this system, besides having at least one light source and a magnetic energy source, also comprises devices to adjust and/or modulate the frequencies and/or the phases and/or the amplitudes of the light and/or the magnetic field so that resonances and/or interferences may be obtained in the biological cellular structure.

The magnetic energy also ensures that the light energy penetrates deeper into the tissue and reaches certain cells that with the presently known instruments were not reached or were insufficiently reached.

The effects of electromagnetic fields on a living organism can be explained as follows. Each living organism is an electromagnetic field that, precisely because of its physical properties, is a living creature. All parts of, for instance, a human body, i.e. its very many billion [UK milliard] cells, are built from complex compounds that themselves consist of molecules. Each molecule has its atoms and each atom has its own little electromagnetic field. This so-called little magnet is kept in existence by positively charged protons and there-around rotating negatively charged electrons.

Hormones, vitamins, (trace) elements, lipids, amino acids, carbohydrates, salts, bases, acids, but also water, oxygen, carbonic acid gas and nitrogen have, by their molecular composition, a proper chemical identity from the periodic system of elements. In addition, they have a specific electromagnetic field or charge, which is built up and composed by the corresponding atoms. One could state that the sum of the electrical charge of each atom in a molecule gives such molecule a specific vibration. We call this the specific vibration frequency or resonance frequency. Consequently, cells, tissues and organs also have electromagnetic properties.

Besides its built-in reinforcement structures, the cell wall also has specific filtration functions. Only very special molecules are assisted inwardly or outwardly, so that the quality of the inside of the cell, the cytoplasm, is preserved and a certain pressure and cell shape is maintained. For instance, a reaction between a hormone and a cell receptor is determined by the fact that both have a mutually compatible vibration. If one of the vibrations weakens, the reaction will take place only partially.

To put it simply, the voltages (potentials) at the inside and outside of the cell wall form the motor of the transport mechanisms through the cell wall of, for instance, ions, food, waste products and cell products. In addition, growth, cell division and cell movement processes can only take place if the correct transport means and membrane potential are present. Magnetic fields influence this potential. In a similar manner, also smaller units such as tissues, cells and cell organelles may obtain 'misinformation' in case of turning magnetic fields or alternating magnetic fields. Precisely what tissue and what process will be influenced depends on factors such as the type of magnetic field and the frequency of its alternations.

In a conductive structure, each change in the electromagnetic field will induce a small electric current, and a voltage difference will be created between the extremities of such structure. In other words, the structure becomes polarized. Some parts within the structure can then also become polarized. The larger or the longer the structure, the larger the voltage difference can become. Basically, elongated structures will operate very well as an antenna for the electromagnetic fields. Hence, basically, structures such as long nerve ends, gliascheden, liquid cavities in the brain and spinal cord and lymph and blood vessels can serve as 'receivers'.

Most living organisms also have a kind of detector for magnetic fields, namely iron-containing ferritin that is especially useful for our orientation.

We often see from experiments that we can only produce the studied effects when the frequency lies within a rather narrow window. Furthermore, such influencing may have either a stimulating or a limiting effect. It is exactly this kind of influencing that we look for with the system in accordance with this invention.

By creating resonances and/or interferences in specific cells, we can influence biological cellular structures in order to obtain a specific therapeutic effect.

Natural oscillations can be observed in a vast range of organisms and tissues, and at very different frequencies, such as protein molecules and protein structures in animal cell walls (millions of Hertz), cell walls with their contractile protein filaments (a few thousand Hertz), some neurones that operate as 'biological clock' (a few Hertz).

The system in accordance with this invention preferably comprises two different light sources, called a first and a second light source, whilst the second light source is capable of generating light that is essentially more coherent than the light from the first light source.

Such system has the advantage that it works even more efficiently within a yet broader field of application. Indeed, when the system is applied to cellular structures of a human or an animal, we observe that, by using two light sources with different coherence, both the received stimuli (by one light source) and the response from the brain (by the other light source) are reinforced according to the well-known principle of the complex-reflex method.

Said first light source can for instance be a full-spectrum lamp. The second light source can for instance be a LED light source that generates mainly coherent light.

In a very preferred configuration, the system comprises devices to use alternately and/or with a phase shift light from the first light source and light from the second light source. This enables triggering specific actions (reflex actions of the neurotransmitters) on specific cells (photoreceptors and cyton cells) and tissues, in which certain biochemical processes are strongly influenced, such as acid-base management and the $Ca^{++}$ channels. Influencing the acid-base management may have an analgesic effect that for instance may produce some pain relief through the stimuli of the endorphins in the skin.

In addition, by photon penetration and modulation, the immune response will be reinforced both at biological cellular and hormonal level, so that, through a correction of the hormonal (endocrine) and emotional imbalance, the body's defense mechanism can react optimally to symptoms of stress, pressure and fatigue.

We obtain a very efficient system if it also is capable of generating pulsing magnetic fields.

By this, by means of specific weak electromagnetic fields, we can perform a bio-stimulation at skin level, by which cell regeneration is strongly stimulated and the tissues, for instance absorb more oxygen. This may stimulate the healing of wounds by, for instance, stimuli of the infiltrations of neutrophils, macrophages, and the formation of Scavenger cells that in turn take care of the evacuation of infectious micro-organisms.

The whole rearranges the disturbed electrical poles of the cell membrane (positively and negatively charged particles), by which the enzymes and their receptors form stimuli for the metabolism and for the creation of energy reserves at cellular level by influencing the mitochondria and stimuli of the ATP, which in turn feeds the cellular chemical processes, in particular by modification of the cellular membrane potential.

The system becomes even more efficient and especially easy to use within its very broad field of application if it also comprises devices to have the frequencies of the magnetic field pulses and/or the light source pulses vary automatically in accordance with a predetermined pattern and/or within a predetermined range, so as to obtain said resonances and/or interferences.

In another preferred configuration, the system also comprises devices to polarize the light coming from the first light source and/or the light coming from the second light source.

By such polarisation, one component (the electrical component of the electromagnetic component) of the light is eliminated. By this organizing effect of the polarisation, we succeed in influencing biochemical processes through the skin nerves, in which especially mechanoreceptors, neuroreceptors, thermal receptors, chemical receptors, light receptors or the acid-base changes are influenced or the $Ca^{++}$ channels and neurotransmitters are stimulated.

The second light source comprises preferably one or several LED light sources that are capable of generating single-phase light.

The system in accordance with this invention is preferably configured to generate a therapeutic effect in a human or animal body.

To further explain the technical properties and operation of this invention and to indicate additional advantages and peculiarities of it, a more detailed description of an instrument in accordance with this invention follows below. However, we insist on the fact that nothing in the description hereunder may be interpreted as a limitation of the claimed patent rights or of the field of application of the system in accordance with this invention.

In this detailed description, reference is made to the enclosed drawings by means of numbers. These drawings are:

DETAILED DESCRIPTION OF THE PREFERRED EMBODIMENTS

Figure 1A:
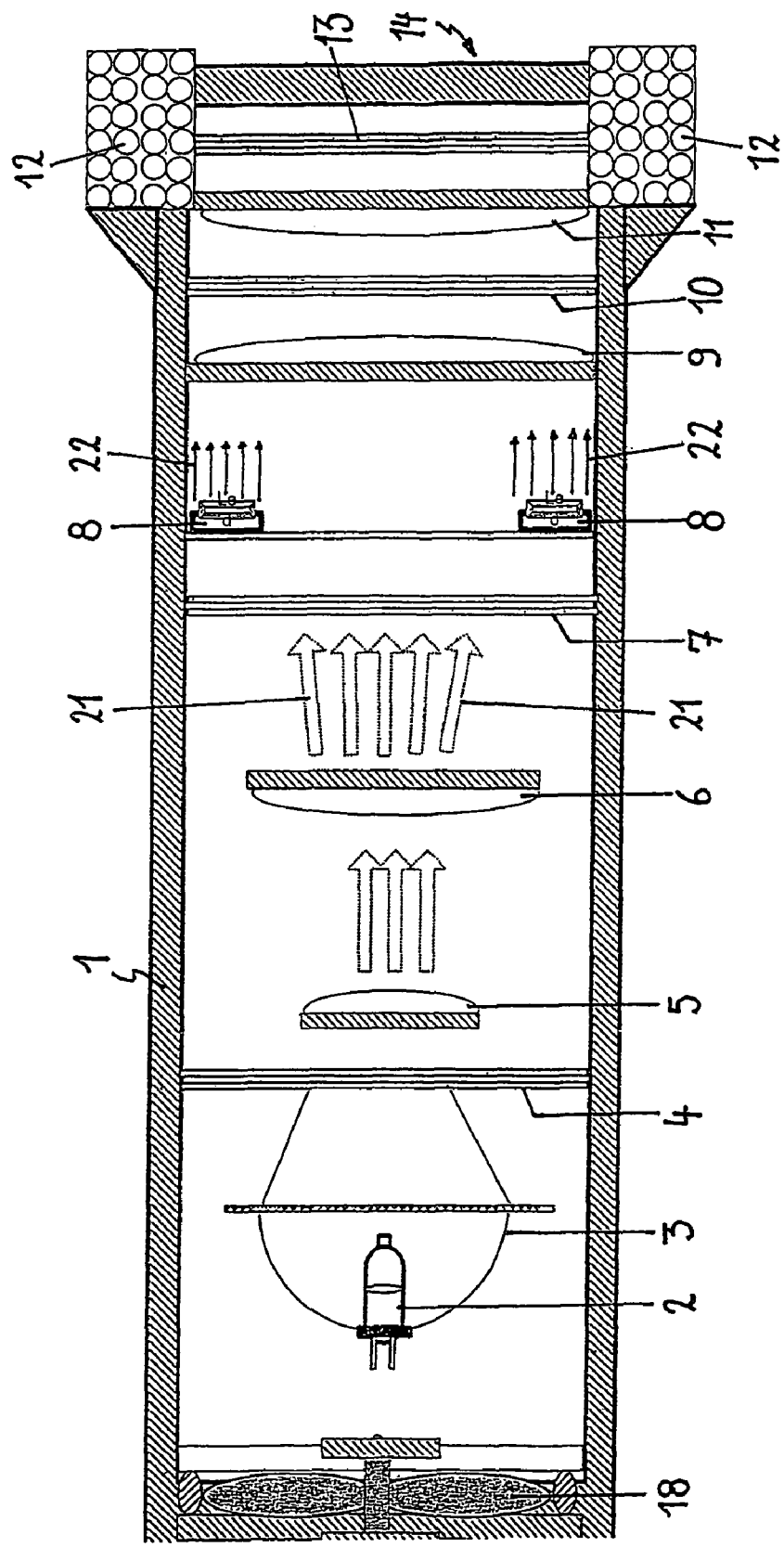
FIGS. 1a and 1b, which show a schematic cross-section of the casing with light sources and magnetic energy source for two different configurations of an instrument in accordance with this invention.

In a first specific configuration (see FIG. 1a), the instrument in accordance with this invention comprises an elongated casing (1) with a open side (14). In this casing (1), a broad-spectrum lamp (2) with reflector (3) is provided. Between this lamp (2), a source of incoherent light, and the open side (14) of the casing (1) we find in succession in the casing (1): an infrared filter (4), a first (5) and a second lens (6), a spectrum filter and/or colour filter (7), a series of LEDs arranged in a ring (8), a third lens (9), a polarisation filter (10), a fourth lens (11), an electromagnetic coil (12) and a protective lens (13) with optimized diaphragm.

A second specific configuration (see FIG. 1b) differs from the first one in that the broad-spectrum lamp (2) is provided with a closed reflector (15) with lens (15a), and in that between the infrared filter (4) and the spectrum filter (7), the first (5) and second lens (6) are replaced by an integrator (16) and one single lens (17). The closed reflector (15) serves to bring the light bundled and with the desired width forward, through reflection on the aluminium sheath, so that we obtain maximum efficiency on the surface that we wish to illuminate.

The broad-spectrum lamp (2) is in both configurations capable of generating a power density of at least 15 mW/cm and a light energy with a value of at least 4 Joule per minute and per cm.

Figure 1B:
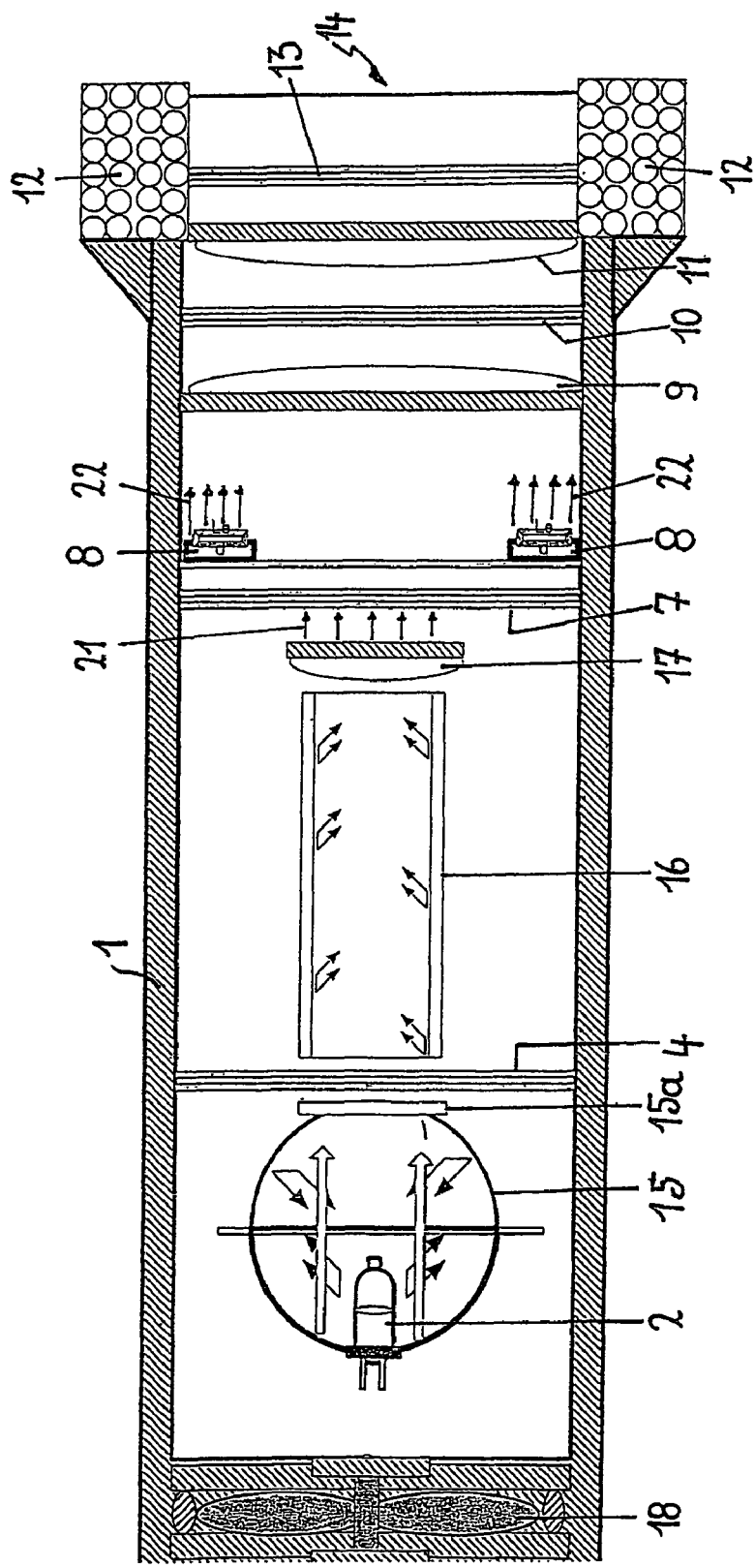
Figure 2:
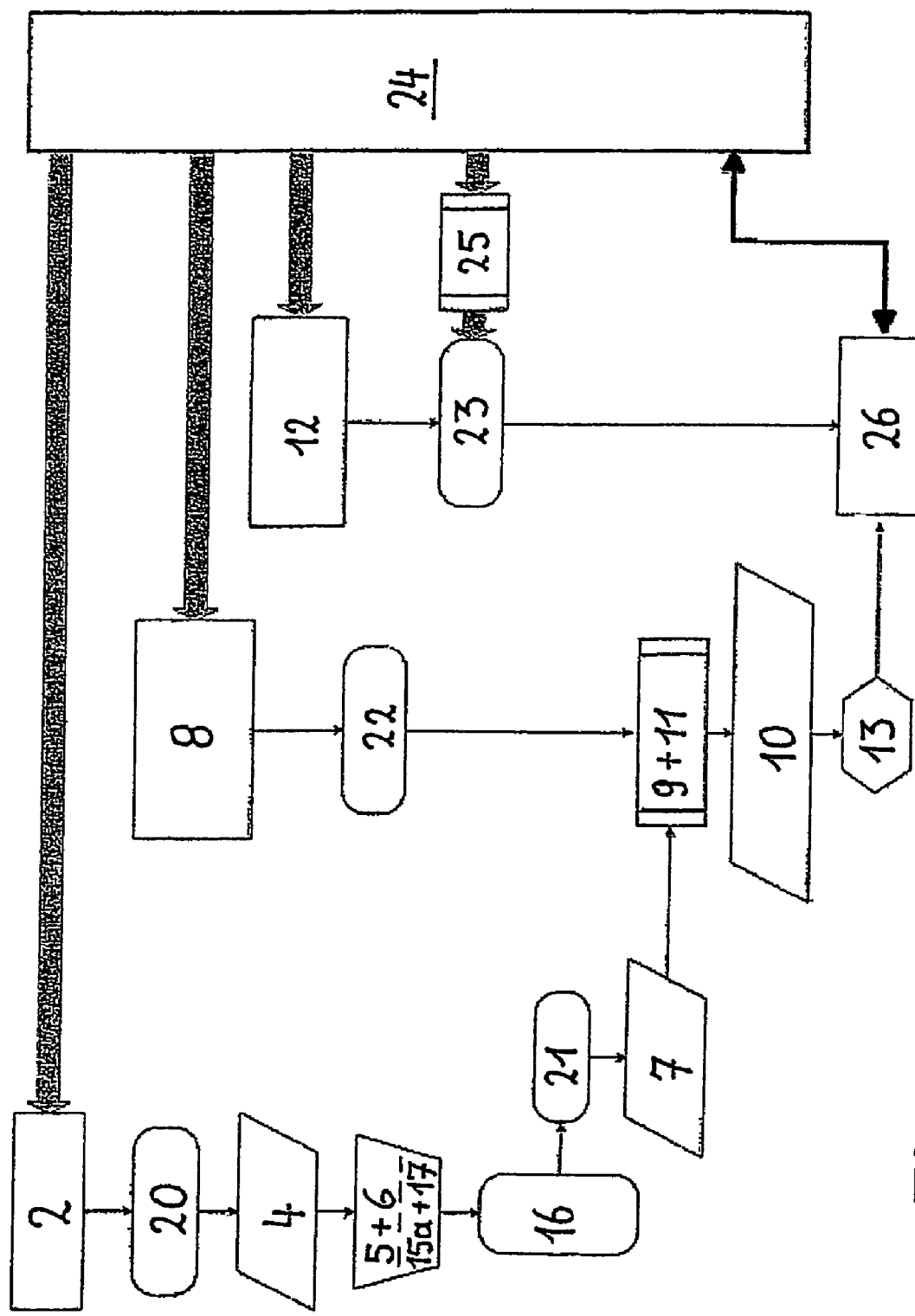
FIG. 2, which illustrates by a block diagram the operating principle of the instrument in accordance with the invention.

The working of the instrument can be further illustrated by means of FIGS. 1a, 1b and 2. The broad-spectrum lamp (2) delivers incoherent light (20) that is filtered in the infrared filter (4) and bundled by the first (5) and the second lens (6) (in the configuration in accordance with FIG. 1a) or by the integrator (16) and lens (17) (in the configuration in accordance with FIG. 1b), so that a bundle of homogenous light (21) is obtained, which is mixed with the coherent light (22) coming from the LEDs (8) by means of the pair of lenses (9), (11). This light is polarised by the polarisation filter (10).

The light coming from the broad spectrum-lamp (2) and the light coming from the LEDs (8) is preferably used alternately. Polarisation preferably takes place with a Brewster polariser or a light transmission system. The light leaves the casing (1) via a protective lens (13) with optimized diaphragm, which ensures that the exiting light bundle can cover a specific surface, in which stray light is eliminated to the maximum possible extent by cutting. The inside of the casing (1) is cooled by means of a fan (18) installed behind the lamp (2).

At the same time, a pulsing magnetic field (23) is generated by means of the electromagnetic coil (12). This magnetic field (23) is used together with the light energy so that the light waves operate as a carrying wave for the magnetic pulses. This is finally the actual end product (26) that leaves the casing and which is used to influence a biological cellular structure.

Meanwhile, the light sources (2), (8) and the electromagnetic coil (12) are controlled by a control system (drive) (24), in order to adjust its frequencies and/or phases and/or amplitudes, so that resonances and/or interferences may be obtained in a treatable biological cellular structure. In FIG. 2, modulation is represented by block (25).

This control system (24) fulfills in particular the following functions in the instrument: pulse wave modulation, dimming and triggering and control of the oscillators (39) and the cooling fan (18).

Figure 3:
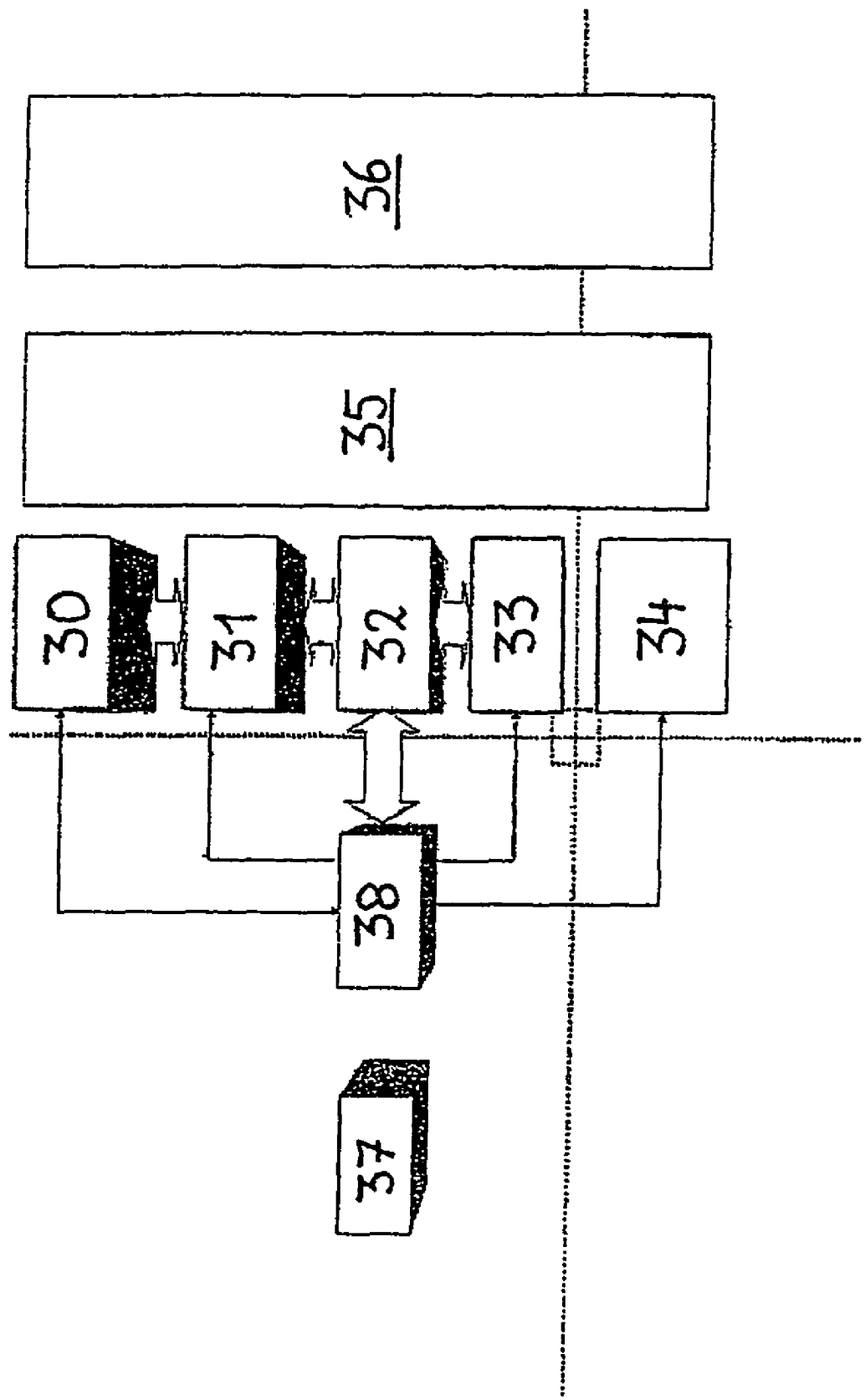
FIG. 3, which shows by a block diagram the different components of the electronic part of the instrument in accordance with the invention.

For this, the control system (24) comprises a microcomputer system with the following components (see FIG. 3). An input module (30) and a screen module (31) for the user, a PC interface module (32), namely RS 232 or USB, a card reading module (33), a sound module (34), an oscillator module (35), drive circuits/dimmer circuits (36), a power supply (37) and an MC microcontroller (38).

Figure 4:
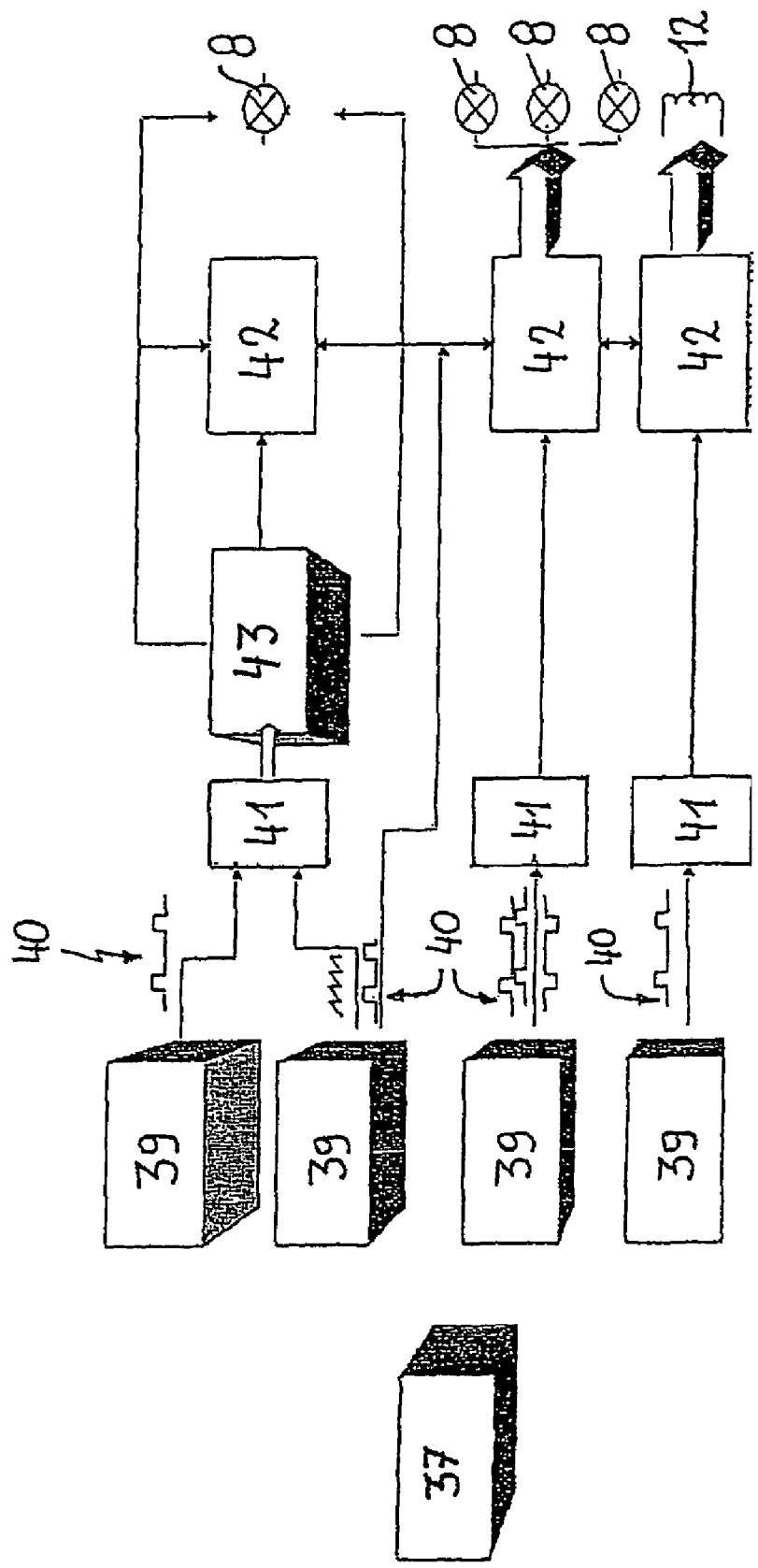
FIG. 4, which presents by a block diagram the oscillator modules and the trigger generators of the instrument in accordance with the invention.

The oscillator module (35) comprises (see FIG. 4) a series of oscillators (39) that are capable of generating square of saw-tooth pulses, by which, through a number of pulse width modulators (41) and trigger generators (42) the LEDs (8) and the electromagnetic coil (12) are driven. The trigger generators (42) co-ordinate the control of the different light sources (2), (8). FIG. 4 also shows the power supply (43) and next to it the pulse width modulator (41) of the drive circuits/dimmer circuits (36).

The microprocessor modules control both the broad-spectrum light source (2) and the LEDs (8). To fulfill its function properly, the microcomputer has at least a bus system, a memory, a timer/counter, a number of input/output channels, a PC interface bus, a control system and a program that coordinates and monitors the whole.

The electronic part can be programmed to automatically generate and run through a pattern of specific frequencies and thus, by means of precision settings, generate resonances in the cellular structure of tissues and bio-cellular matrix, in general in a biological cellular structure.

The two different light sources can be driven separately and combined in accordance with a specific modulation pattern and this synchronously with the employed magnetic fields, this in order to modify for instance the reflection and absorption behaviour of the treated tissue at a specifically to be set resonance frequency, by which very deep tissue penetration can be obtained. An additional modulation takes care of the cellular information transfer.

To mix the light of the first and the second light source, the instrument can be provided with an integrator pipe or a fibre optic channel (not shown in FIGS. 1a and 1b). When a fibre optic channel is used, we obtain a very pronounced flank cut in the UV and infrared light frequency ranges. By this, any heating of the treated biological cellular structure is prevented. Of course, this enhances the safety and the user friendliness of the instrument.

To obtain an efficiently working instrument, it is important that the emitted light is homogenous over a relatively large surface, this in order to reach at once the largest possible surface of the to be treated cellular structure. By use of the first (5) and the second lens (6) in the instrument in accordance with FIG. 1b, we ensure that this surface is sufficiently large. The lens (5) is used to draw the central homogenous part of the light out of the light bundle. Then, by means of another lens (6), this homogenous part is enhanced to a light bundle that is homogenous over a relatively large surface.

For instance, to be able to work efficiently in case of wound treatment, we will ensure that the light is homogenous on an a surface of at least 100 $cm^2$. For other applications for instance, it will be indicated to have a homogenous light on a surface that corresponds with the size of the head or of another body part of a person or animal.

The instrument in accordance with this invention can be used in a large variety of fields of application, such as obtaining beneficial therapeutic effects for arthritis/arthrosis. In this case, the instrument is automatically set to a base frequency of about 4 Hz, and an inflammation limiting effect is obtained at a frequency of about 6 Hz.

The instrument can also be used to obtain for instance beneficial effects in cases of tendinitis or acute inflammations. Then, the instrument is automatically set to a pain relieving frequency about 4 Hz. In this case, the inflammation limiting frequency is also about 4 Hz.

For the above-mentioned frequency settings, a margin of error of about 10% is admissible.

The system in accordance with the invention can be used to influence any biological cellular structures and to realise a wide range of therapeutic or other beneficial effects. The term influencing/to influence must be interpreted in its most broad significance, in which both temporary and permanent effects, phenomena or modifications in the biological cellular structure must be considered 'an influence'.

Within the framework of this invention, the instrument in accordance with this invention can be realised in many configurations that strongly differ from each other, according to, for instance, the envisaged field of application or the desired effect.

The invention claimed is:

1. A system for influencing of a biological cellular structure that makes use of a combination of light energy and magnetic energy, characterized in that this system comprises, a first light source comprising a full-spectrum lamp and a second light source comprising one or more LED light sources that are capable of generating single-phase light that is essentially more coherent than the light of the first light source, devices which permit operation of the light coming from the first and the second light source alternately or with a phase shift, a magnetic energy source, and devices which permit selective and independent adjustments and modulations of the frequencies and the phases and the amplitudes of the emitted light and the emitted magnetic field to coordinate the emitted light and the emitted magnetic field to obtain resonances or interferences in the biological cellular structure.

2. A system for influencing of a biological cellular structure, according to claim 1, characterised in that the system is capable of generating pulsing magnetic fields.

3. A system for influencing of a biological cellular structure, according to claim 2, characterised in that the system comprises devices to polarise the light emitted by the first and the second light sources.

4. A system for influencing of a biological cellular structure, according to claim 1, characterised in that said devices are capable of having the frequencies and the phases and the amplitudes of the magnetic field pulses and the light source pulses vary in accordance with predetermined patterns and within predetermined ranges in order to obtain said resonances or interferences.

5. A system for influencing of a biological cellular structure, according to claim 1, characterised in that it is capable of generating a therapeutic effect in a human or animal body.

* * * * *